United States Patent
Tartre

(10) Patent No.: US 6,289,714 B1
(45) Date of Patent: Sep. 18, 2001

(54) METHOD FOR TESTING SOIL CONTAMINATION, AND PROBE THEREFOR

(76) Inventor: André Tartre, 540, rue Morin, Longueuil, Québec (CA), J4L 3Z7

( * ) Notice: Subject to any disclaimer, the term of this patent is extended or adjusted under 35 U.S.C. 154(b) by 0 days.

(21) Appl. No.: 09/412,579

(22) Filed: Oct. 5, 1999

Related U.S. Application Data

(63) Continuation-in-part of application No. 09/118,888, filed on Jul. 20, 1998, now Pat. No. 5,992,213, which is a continuation-in-part of application No. 08/718,505, filed on Oct. 4, 1996, now Pat. No. 5,786,527.

(51) Int. Cl.[7] ............... G01N 1/24; G01N 1/00; G01N 31/00; G01N 33/24
(52) U.S. Cl. ............ 73/19.01; 73/19.12; 73/864.74; 73/864.33; 73/864.43; 175/59; 175/64
(58) Field of Search ............... 73/19.01, 19.12, 73/864.74, 864.43, 864.41, 864.81, 864.33, 31.07; 175/60, 64, 21, 59

(56) References Cited

U.S. PATENT DOCUMENTS

| | | |
|---|---|---|
| 3,180,983 | 4/1965 | Hall, et al. . |
| 3,685,345 | 8/1972 | Wise . |
| 3,714,811 | 2/1973 | Daigle et al. . |
| 3,857,289 | 12/1974 | Wise . |
| 4,335,622 | 6/1982 | Bartz . |
| 4,452,091 | 6/1984 | Richers . |
| 4,804,050 | 2/1989 | Kerfoot . |
| 5,478,452 | * 12/1995 | Chriswell et al. ............ 204/153.2 |
| 5,479,814 | * 1/1996 | Rehn ............................. 73/19.01 |
| 5,518,931 | * 5/1996 | Plessers ........................... 436/52 |
| 5,639,956 | * 6/1997 | Christy .......................... 73/19.01 |
| 5,712,421 | * 1/1998 | Raisanen ....................... 73/19.01 |
| 5,786,527 | 7/1998 | Tartre . |
| 5,992,213 | * 11/1999 | Tartre ............................ 73/19.01 |

* cited by examiner

Primary Examiner—Hezron Williams
Assistant Examiner—David J. Wiggins
(74) Attorney, Agent, or Firm—Francçois Martineau

(57) ABSTRACT

The method is used for locally testing underground soil contamination by determining the generation rate of a first contaminant fluid in porous soil. The method includes the steps of making a hole of known dimensions in the soil, with the hole defining a first and a second spaced-apart portions; covering the hole, so as to define a closed volume in the hole; constantly injecting a second fluid in the hole at a constant given flow rate at said first portion of the hole, while simultaneously collecting fluid samples at the above-mentioned constant given flow rate at the second portion of the hole; measuring the concentrations of the first contaminant fluid from the fluid samples collected at known time intervals; and computing the generation rate of the first contaminant fluid, from the known volume of the hole and from the concentrations previously measured and originating from samples collected at the known time intervals. The probe used to carry out the above-described method has a rigid hollow body in which a semi-rigid tube is axially slidable. The probe can be driven through the ground and then partially retracted, to form a hole of known dimensions. The flexible tube is axially displaced so that its lower bored extremity is positioned near the bottom end of the hole, while the hollow rigid body of the probe has an annular opening about the tube at the upper end of the hole. The second fluid can then be circulated in the hole between the lower end of the tube and the annular opening of the probe rigid main body.

10 Claims, 4 Drawing Sheets

METHOD FOR TESTING SOIL CONTAMINATION, AND PROBE THEREFOR

CROSS-REFERENCE DATA

The present application is a Continuation-in-Part of U.S. patent application Ser. No. 09/118,888 filed by the present applicant on Jul. 20, 1998 and granted under U.S. Pat. No. 5,992,213 on Nov. 30, 1999; the latter being a Continuation-in-Part of U.S. patent application Ser. No. 08/718,505 filed by the present applicant on Oct. 4, 1996 and granted under U.S. Pat. No. 5,786,527 on Jul. 28, 1998.

FIELD OF THE INVENTION

The present invention relates to a method for testing soil contamination in situ.

BACKGROUND OF THE INVENTION

The parent U.S. application Ser. No. 09/11 8,888 (hereafter the '888 application) filed by the present applicant discloses a method for testing the soil contamination by ejecting a circulation fluid in the soil, with a very small proportion of a tracer fluid. Fluid samples are simultaneously collected wherein contaminant fluid concentrations and tracer fluid concentrations are measured and used for computing the effective flow rate Q', in the affected soil volume. The tracer gas is used to circumvent the fact that the value of the affected soil volume is not known. With the effective flow rate Q', the generation rate G of the contaminants in the soil can be computed. With this method according to the '888 application, the use of a tracer gas is compulsory.

Also, according to the method described in the '888 application, the circulation fluid is ejected into the soil by the probe at a greater flow rate than the fluid intake flow rate. This results in a local increase of the quantity of fluid near the probe tip, which creates fluid pressure differentials in the soil. The contaminant fluids will consequently be prone to migrating in the soil according to fluid pressure gradients instead of migrating according to fluid concentration gradients.

U.S. Pat. No. 3,685,345 issued in 1972 to Harold L. Wise, commented in the Background of the Invention section of the '888 application, shows a soil sampling apparatus including an outlet tube and an inlet tube each having an opened lower extremity located near the bottom of a hole having been drilled in the ground. A circulation fluid is ejected from the outlet tube lower opening, and the circulation fluid mixed with a proportion of contaminants is collected by the inlet tube lower opening. However, in the Wise patent, the entire hole is not subjected to the circulation fluid, since the fluid ejection and collection both occur near the lower extremity of the hole. Thus, it is not possible with the method described in the Wise patent, to determine an approximate affected soil volume to be used to compute the generation rate of contaminants in the soil. In any event, the object of the Wise method is not to verify the contaminant generation rate, but to verify the concentration of the contaminant fluid.

OBJECTS OF THE INVENTION

It is an object of the present invention to provide a method for testing soil contamination without the use of a tracer fluid, and thus by ejecting only a single fluid in the soil.

It is an object of the present invention to provide a method for testing soil contamination by injecting a circulation fluid in the soil, while maintaining a substantially constant fluid pressure in the area where testing occurs.

It is a further object of the present invention to provide a probe for testing soil contamination.

SUMMARY OF THE INVENTION

The present invention relates to a method for locally testing underground soil contamination by determining the generation rate of a first contaminant fluid in porous soil, said method comprising the steps of:
a) making a hole of known dimensions in the soil;
b) covering the hole, so as to define a closed cavity of known volume;
c) constantly ejecting a second fluid in said cavity, at a constant given flow rate;
d) simultaneously continuously collecting fluid samples from said cavity at a location therein away from where said second fluid is ejected, at said constant given flow rate, to create a circulation flow of the second fluid in the entire cavity;
e) measuring the concentrations of said first contaminant fluid from at least three of said fluid samples collected at known time intervals; and
f) computing the generation rate of said first contaminant fluid, from the known volume of the cavity and from the concentrations measured in step (e) originating from samples collected at the known time intervals.

The present invention also relates to a method for locally testing underground soil contamination by determining the generation rate of a first contaminant fluid in porous soil, said method comprising the steps of:
a) making an elongated hole of known dimensions in the ground soil, with the hole defining a first and a second spaced-apart end portions;
b) covering the hole, so as to define a closed cavity of known volume;
c) constantly ejecting a second fluid in said cavity, at a constant given flow rate, near either one of said upper and lower end portions of said cavity;
d) simultaneously continuously collecting fluid samples from said cavity, at said constant given flow rate, near the other one of said first and second end portions of said cavity;
e) measuring the concentrations of said first contaminant fluid from at least three of said fluid samples collected at known time intervals; and
f) computing the generation rate of said first contaminant fluid, from the known volume of the cavity and from the concentrations measured in step (e) originating from samples collected at the known time intervals.

Preferably, the method further comprises, between step (a) and step (b), the step of inserting into the hole a hollow probe, wherein said probe extends from said cavity first portion to said cavity second portion and has a second fluid outlet opening at said cavity first portion and a first fluid inlet opening at said cavity second portion, said outlet and inlet openings being respectively connected to inlet and outlet conduits, the fluid ejection in step (c) being accomplished through said outlet conduit in said hollow probe and the fluid collection in step (d) being accomplished through said inlet conduit in said hollow probe.

Preferably, the method further comprises before step (a), the steps of driving through the soil a hollow probe and partially retracting said probe to make the hole according to step (a) and to simultaneously cover the hole according to step (b), the probe then extending from said cavity first portion to said cavity second portion and having a second fluid outlet opening at said cavity first portion and a first fluid inlet opening at said cavity second portion, said outlet and inlet openings being respectively connected to inlet and outlet conduits, wherein the fluid injection in step (c) is accomplished through said outlet conduit in said hollow probe and wherein the fluid collection in step (d) is accomplished through said inlet conduit in said hollow probe.

Preferably, said second fluid is a substantially inert gas, and advantageously this second fluid is a gaseous fluid selected from the group comprising helium, argon and nitrogen.

Preferably, said known time intervals are regular time intervals.

The present invention further relates to a probe for testing soil contamination, comprising:

a rigid main body having an inner conduit defining a lower opening and a first and a second top openings;

an inner tube coaxially located inside said inner conduit and of lesser diameter than said inner conduit, so as to allow fluid passage in said inner conduit about said tube, said inner tube extending upwardly out of said rigid main body through said first top opening and defining a top opening outwardly of said rigid main body, said inner tube further defining a lower opening;

a seal mounted to said main body at said inner conduit first top opening, to prevent fluid passage out of said inner conduit through said inner conduit first top opening about said inner tube;

wherein either one of said inner conduit second top opening and said inner tube top opening is adapted to be connected to a circulation fluid source, while the other one of said inner conduit second top opening and said inner tube top opening is adapted to be connected to a fluid sample collecting device; and wherein said inner tube is axially slidable in said inner conduit between a retracted position, in which said inner tube lower opening is located inside said inner tube, and an extracted position, in which said inner tube lower opening projects out of and spacedly beyond said inner tube lower opening, whereby fluid from said circulation fluid source is destined to circulate between said tube lower opening and said casing conduit lower opening which are spaced-apart.

Preferably, said tube is made of a semi-rigid plastic material.

Preferably, said tube lower opening is a number of spaced apart holes made at a bottom end portion of said tube.

DETAILED DESCRIPTION OF THE EMBODIMENTS

Figure 1:
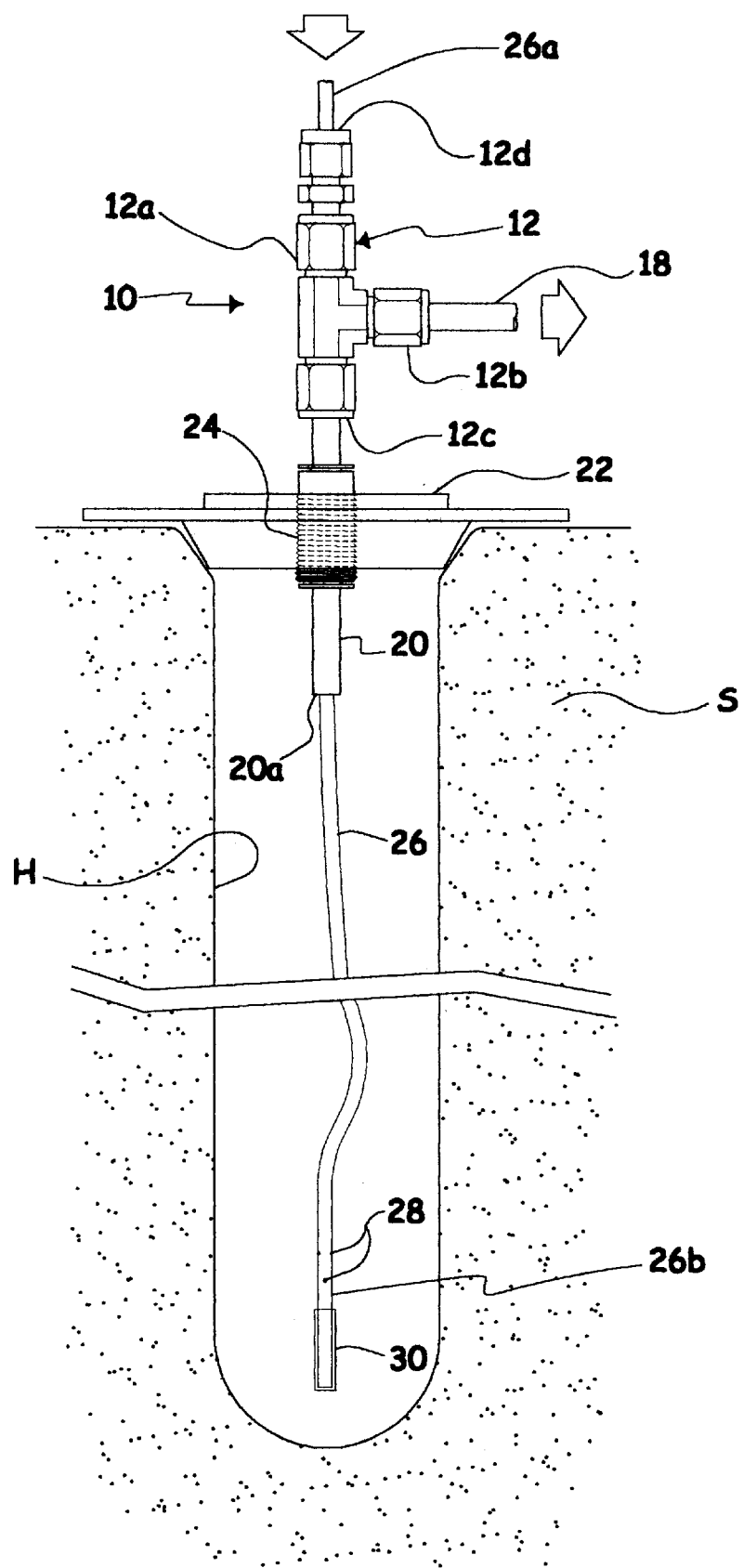
FIG. 1 is a side elevation showing a first embodiment of a probe used to carry out the method according to the present invention, the probe being partly inserted in a hole made in the ground.
Figure 2:
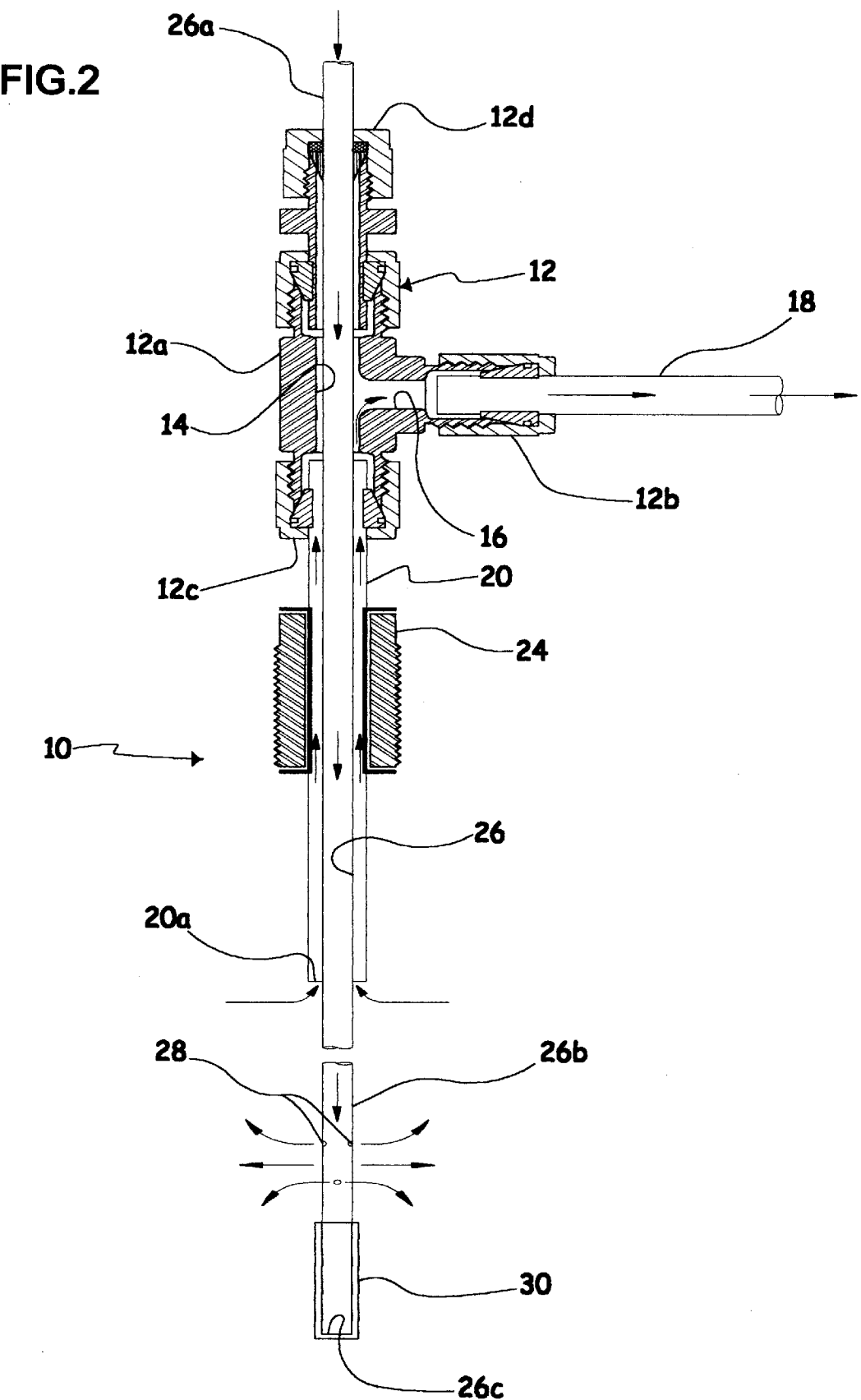
FIG. 2 is an enlarged partly broken detailed cross-sectional view of the probe of FIG. 1.

FIG. 1 shows an upwardly open ground cavity or hole H made in porous soil S in which a first embodiment of a probe 10 used to carry out the method according to the present invention has been partly inserted. The hole H may have been made in any appropriate manner, e.g. with an auger. FIGS. 1 and 2 show that probe 10 comprises a rigid hollow T-adaptor 12 similar to the one described in the parent '888 application and which includes a vertical main body 12a and a transversely projecting side arm 12b. A first inner conduit 14 vertically extends in the T-adaptor main body 12a, and a second transverse conduit 16 located in side arm 12b is in fluid connection with first conduit 14 so as to form a T-shaped inner conduit 14, 16. A pipe 18 connected to the T-adaptor transverse arm 12b allows fluid connection between side conduit 16 and a remote fluid sample collecting device (not shown) of known construction, e.g. a commercially available testing device which simultaneously collects the fluid samples and measures the concentrations of desired fluids therein, the testing device visually providing the measured concentrations.

A semi-rigid elongated sleeve 20, e.g. made of a suitable fluid-tight (e.g. plastic) material, is carried at the lower end 12c of T-adaptor 12, sleeve 20 being in fluid connection with volume.

A semi-rigid inner tube 26, e.g. made of a suitable fluid tight (e.g. plastic) material, extends coaxially inside first conduit 14. The upper end portion 26a of inner tube 26 upwardly extends out of and beyond T-adaptor 12, with the latter being sealed about inner tube 26 at its upper end portion 12d. The tube upper end portion 26a is fluidingly connected to a suitable remote circulation fluid source (not shown). Tube 26 further extends into and downwardly well beyond sleeve 20, the lower end portion 26b of inner tube 26 being provided with a number of peripherally disposed radial bores 28 to allow fluid flowing in tube 26 to be redirected radially out through bores 28 all around the tube lower end portion 26b. A cap 30 seals the lower extremity 26c of tube 26 spacedly under bores 28. Inner tube 26 has a smaller diameter than the inner surface of sleeve 20 and of inner conduit 14, so as to loosely fit therein to allow fluid to flow in the annular area located between tube 26 and sleeve 20 and between tube 26 and inner conduit 14.

In use, probe 10 is positioned as shown in FIG. 1, i.e. with cover 22 resting on the top edge of hole H while the lower end portion 26b of tube 26 freely hangs near the bottom pipe 18 to be respectively connected to a circulation fluid source and to a sample collecting device. A circulation fluid is continuously ejected into the hole H through inner tube 26 and out through bores 28, while fluid samples are continuously collected through the annular lower open mouth 20a of sleeve 20 to be carried through elbowed inner conduit 14, 16 and through pipe 18 into the sample collecting device. The concentration of one or more contaminants can be measured in a known fashion from the fluid samples thus collected.

The position of the tube lower end portion 26b relative to T-adaptor 12 and to the sleeve lower mouth 20a can be selectively adjusted by axially forcing tube 26 inside conduit 14 against the peripheral friction between the T-adaptor upper seal 12d and the tube 26. Thus, the tube lower end portion 26b can be positioned at or near the bottom of holes H of different depths, out of sleeve 20 and spacedly away from lower mouth 20a.

Figure 3:
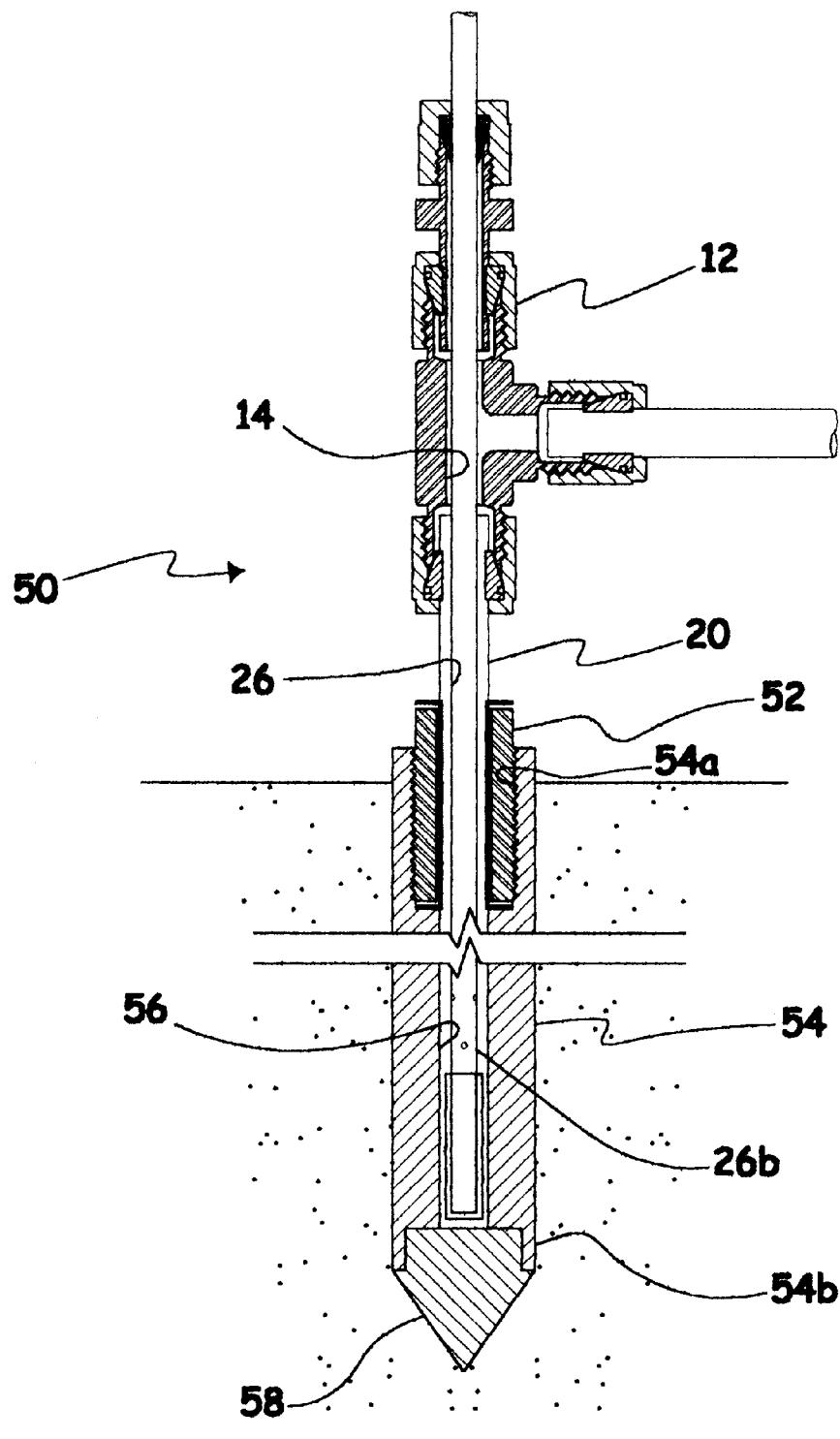
FIG. 3 is a cross-sectional side-elevation of a second embodiment of a probe used to carry out the method according to the present invention, the probe being inserted into the ground in a first contracted ground-engaging condition.
Figure 4:
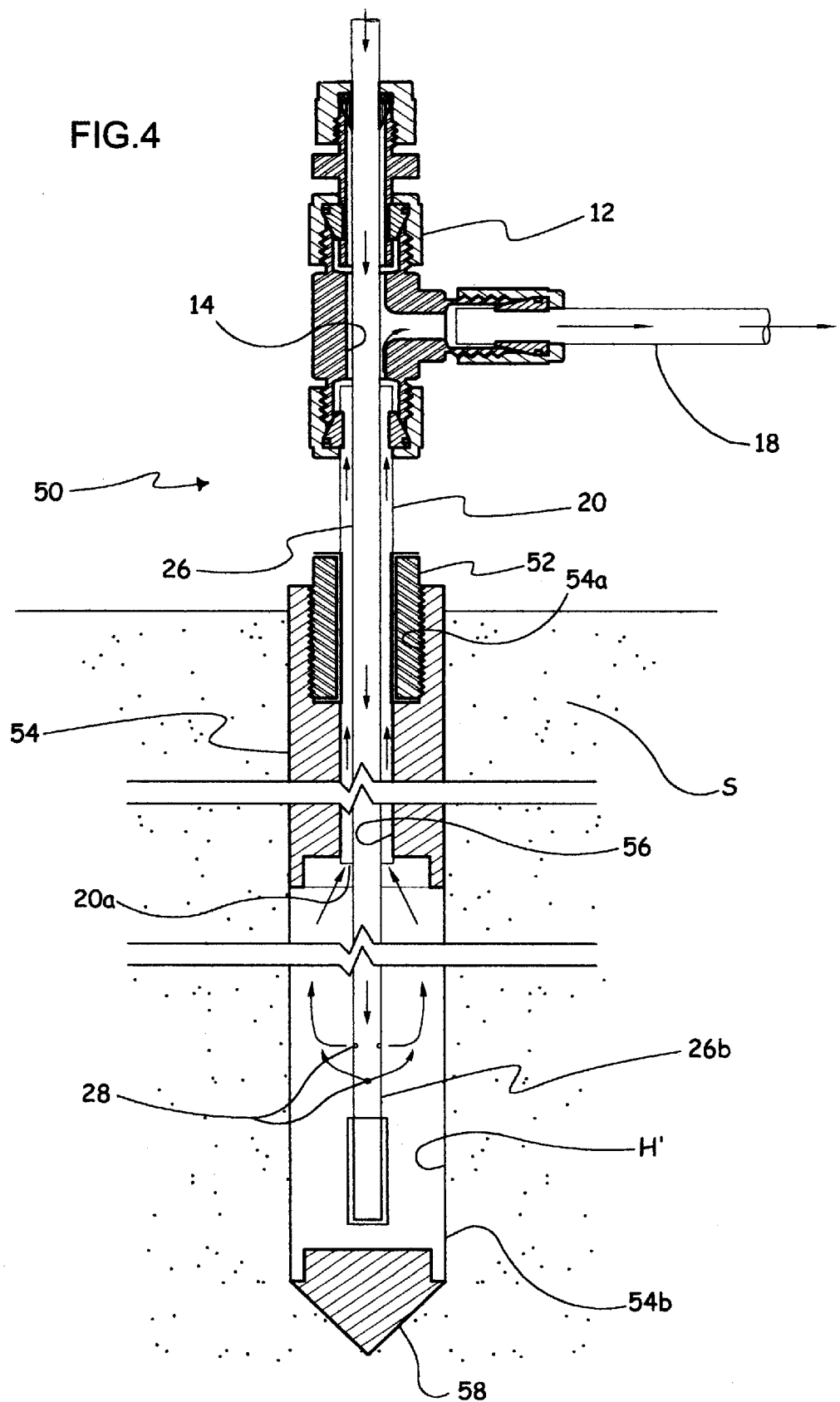
FIG. 4 is a view similar to FIG. 3, but at a slightly enlarged scale and with the probe being shown in a second extended operative condition, with arrows suggesting the direction of the fluid circulation flow in the probe conduits and in the cavity formed by the partly retracted probe rod.

FIGS. 3 and 4 show an alternate embodiment of a probe 50 used to carry out the method according to the present invention, which is similar to the probe of FIGS. 1 and 2 except as noted below. Probe 50 includes a threaded ring 52, which may be identical to or different from ring 24 of the probe 10 of the first embodiment, and which is threadingly engaged by the threaded upper end portion 54a of a hollow annular probe rod 54. Probe rod 54 has an axially extending inner conduit 56 which partly encloses sleeve 20 and tube 26 under ring 52. The lower end portion 54b of probe rod 54 is provided with a self-removable expendable pointed tip member 58 of known construction, also called sacrificial tip.

In use, the probe 50 of the second embodiment is to be forcibly driven through the ground to a desired depth as shown in FIG. 3, with the encasing probe rod 54 preventing undesirable clogging of the small holes 28 of tube 26 with earth. Then, the probe rod 54 is to be upwardly partly retracted from the ground, thus creating a hole H' as shown in FIG. 4, with the sacrificial tip 58 remaining stuck into the soil at the bottom of the hole H, while tube 26 is forcibly axially slidingly displaced inside conduit 14 so that the tube lower end portion 26b remain at or near the bottom of hole H'. The circulation fluid is then ejected through holes 28, while fluid samples are continuously collected through the sleeve annular lower mouth 20a at the upper end of hole H'.

The method for testing the soil contamination according to the invention is the same with both of the above-mentioned probes 10 and 50. Indeed, it can be seen that in both cases, a hole H or H' is created about the portion of probe tube 26 which protrudes outwardly of sleeve 20. The probe lower end portion 26b is located in a spaced-apart fashion relative to the sleeve lower mouth 20a in hole H or H'. More particularly, the tube lower end portion 26b is located near the bottom of hole H or H', while the sleeve bottom mouth 20a is located near the top of the hole H or H'. Thus, the circulation fluid ejected out of holes 28 circulates in hole H, H' where it becomes admixed with a certain proportion of contaminants, and then collected through mouth 20a to be carried to the fluid sample collecting device.

According to the method of the invention, it is important that the fluid samples be collected at a same flow rate than that of the circulation fluid being ejected from the tube lower end portion 2b. Thus, no pressure differential will occur during the soil testing. This is contrary to the method of the '888 application in which the circulation fluid was ejected at a greater flow rate than that of the sample collecting, which created a positive fluid pressure in the affected soil volume surrounding the probe tip. In this old method, the contaminants were subjected to fluid pressure gradients which were prone to affect the migration of the contaminants in the affected soil volume.

With the method of the present invention, however, no positive fluid pressure would be created since the fluid being ejected and the fluid being collected flow at a same given rate. This has two consequences on the present method:
a) The effective fluid volume which is affected by this circulation of fluid can be approximated to that of the volume of the cavity in which the circulation fluid is ejected and from which the sample fluid is collected. Consequently, the value of the affected volume becomes known, which was not the case in the '888 application where a tracer gas was used to circumvent this.
b) Since little or no fluid pressure differentials are created in the affected soil fluid volume, the contaminants will effectively migrate through the solid but porous ground soil surrounding the hole, and into the empty hole fluid volume, following concentration gradients, which is desirable so as to verify the respective generation rates of the contaminants. This was not the case in the '888 application, where positive fluid pressure differentials resulting from the fluid ejection in the soil resulted in the contaminants migrating also along fluid pressure gradients.

From the collected samples, the concentration of the contaminant is measured using known methods, e.g. with a commercially available testing apparatus. It is important that the time intervals between the collection of each measured sample be known, as will be seen hereinafter.

The following equation (1) yields the generation rate G of a contaminant fluid:

Equation No 1

$$G = \frac{Q'\left[C_2 - \left(C_1 e^{\frac{-Q'(t_2-t_1)}{V}}\right)\right]}{1 - e^{\frac{-Q'(t_2-t_1)}{V}}}$$

where Q' is the effective flow rate of the contaminant; $C_2$ and $C_1$ are the concentrations of the contaminant fluid measured from samples collected at two different times; e is the base of the Napierian logarithmic system and equals approximately 2.7182; $(t_2-t_1)$ is the time interval between the collection of the samples whose concentrations are $C_2$ and $C_1$; and V is the affected volume in which the generation rate is to be computed. According to the method of the present invention, the affected volume V is known since it can be approximated to that of the ground cavity in which the probe is inserted, and the measured concentrations and the time interval between two successive sample collecting are also known.

Thus, two unknown variables remain in equation (1), namely the generation rate G and the effective flow rate Q'. To solve this equation, contaminant concentrations measured from samples collected at least at three different times have to be used. Since the generation rate and the effective flow rate remain the same, the generation rate can thus be determined from the two equations resulting from the two different time intervals and the three measured concentrations. Indeed, in addition to equation (1) above yielding the generation rate according to the concentrations $C_1$ and $C_2$ measured at a first and a second times $t_1$ and $t_2$, the following equation (2) yields the generation rate according to the concentrations $C_2$ and $C_3$ measured at the second and third times $t_2$ and $t_3$.

Equation No 2

$$G = \frac{Q'\left[C_3 - \left(C_2 e^{\frac{-Q'(t_3-t_2)}{V}}\right)\right]}{1 - e^{\frac{-Q'(t_3-t_2)}{V}}}$$

For each contaminant, it is thus possible to mathematically compute the generation rate thereof in the fluid volume hole made in the soil, since we have a system of two equations and two unknown variables. The method of the present invention allows the generation rate to be determined without using a tracer gas as was the case in the '888 application. As explained hereinabove, this is done by boring a hole of known dimensions in the ground, and by ejecting a circulation fluid at a flow rate which is equal to the flow rate of the collected fluid intake. Upon measuring the contaminant concentrations from the collected fluid at known collecting time intervals, the generation rate can be computed as detailed in equations (1) and (2).

Preferably, concentrations measured from samples collected at regular time intervals are used, for the purpose of simplifying the mathematical operations.

The probe 50 according to the second embodiment shown in FIGS. 3 and 4 is the preferred device for accomplishing the method according to the present invention. Indeed, it is simple to use since no auger is required, while providing an affected fluid volume (i.e. hole H') of rather precise dimensions, equal to the volume of the retracted portion of probe rod 54, from which the volume of the tube 26 is subtracted.

As described in the parent '888 application, the circulation fluid is preferably an inert gas or a substantially inert gas, so as to prevent chemical reactions from occurring between the injected circulation fluid and one or more chemical components that may be present in the affected soil volume. The circulation fluid may be, for example, helium, argon or nitrogen. Depending on the contaminants which are present in the soil, ambient air can also be used as a circulation fluid, as long as the air is not likely to be included in any chemical reaction with one or another contaminant.

As with the method and device disclosed in the '888 application, the method according to the present invention is used for locally testing soil contamination by determining the generation rate of a first contaminant fluid in porous soil. Preferably the method of the invention is used for testing a soil contaminated by toxic fluids, although a soil contaminated by non-toxic fluids can also be tested. The contaminant fluid can be, for example, methane xylene, carbon dioxide, or any other suitable toxic or non-toxic fluid.

The invention, as previously discussed in the '888 application, is very suitable for measuring the presence of a volatile or a gaseous contaminant. However, it will be understood that the method according to the present invention could also be used with other fluids, including liquids.

Any modifications which do not deviate from the scope of the present invention are considered to be included therein.

For example, it is envisioned that the circulation fluid outlet ports be located near the upper portion of the ground hole, while the fluid collecting inlet be located at the bottom of the hole. In any event, the inlet and outlet ports have to be located in a spaced-apart fashion in the hole to circulate the ejected circulation fluid in the entire volume of the hole for the volume in which the generation rate of the contaminant(s) is computed to be approximated to the fluid volume of the hole made in the ground. Preferably the inlet and outlet ports are positioned near the two opposite extremities of an elongated hole.

Also, although sleeve 20 and tube 26 have been described as being made from semi-rigid plastic material, they could alternately be made of a suitable fluid tight rigid material which would not be reactive with the contaminant fluids under test.

I claim:

1. A method for locally testing underground soil contamination by determining the generation rate of a first contaminant fluid in a porous soil capable of storing a volume of one or more contaminant fluids, this volume yielding corresponding concentrations of said one or more contaminant fluids, said method comprising the steps of:
   a) making a hole of known dimensions in the soil;
   b) covering the hole, so as to define a closed cavity of known volume;
   c) constantly ejecting a second fluid in said cavity, at a constant given flow rate;
   d) simultaneously continuously collecting fluid samples from said cavity at a location therein away from where said second fluid is ejected, at said constant given flow rate, to create a substantially constant circulation flow of the second fluid in the entire cavity;
   e) measuring the concentrations of said first contaminant fluid from at least three of said fluid samples collected at a set of known time intervals; and
   f) computing the generation rate of said first contaminant fluid, from the known volume of the cavity and from the concentrations measured in step (e) originating from samples collected at the known time intervals.

2. A method for locally testing underground soil contamination by determining the generation rate of a first contaminant fluid in a porous soil capable of storing a volume of one or more contaminant fluids, this volume yielding corresponding concentrations of said one or more contaminant fluids, said method comprising the steps of:
   a) making an elongated hole of known dimensions in the ground soil, with the hole defining a first and a second spaced-apart end portions;
   b) covering the hole, so as to define a closed cavity of known volume;
   c) constantly ejecting a second fluid in said cavity to accomplish a desired fluid injection, at a constant given flow rate, near either one of said upper and lower end portions of said cavity;
   d) simultaneously continuously collecting fluid samples from said cavity, at said constant given flow rate, near the other one of said first and second end portions of said cavity;
   e) measuring the concentrations of said first contaminant fluid from at least three of said fluid samples collected at a set of known time intervals; and
   f) computing the generation rate of said first contaminant fluid, from the known volume of the cavity and from the concentrations measured in step (e) originating from samples collected at the known time intervals.

3. A method as defined in claim 2, further comprising, between step (a) and step (b), the step of inserting into the hole a hollow probe, wherein said probe extends from said cavity first portion to said cavity second portion and has a second fluid outlet opening at said cavity first portion and a first fluid inlet opening at said cavity second portion, said outlet and inlet openings being respectively connected to a corresponding inlet conduit and a corresponding outlet conduit, the fluid ejection in step (c) being accomplished through said outlet conduit in said hollow probe and the fluid collection in step (d) being accomplished through said inlet conduit in said hollow probe.

4. A method as defined in claim 2, further comprising before step (a), the steps of driving through the soil a hollow probe and partially retracting said probe to make the hole according to step (a) and to simultaneously cover the hole according to step (h) the probe then extending from said cavity first portion to said cavity second portion and having a second fluid outlet opening at said cavity first portion and a first fluid inlet opening at said cavity second portion, said outlet and inlet openings being respectively connected to a corresponding inlet conduit and a corresponding outlet conduit, wherein the fluid injection in step (c) is accomplished through said outlet conduit in said hollow probe and wherein the fluid collection in step (d) is accomplished through said inlet conduit in said hollow probe.

5. A method as defined in claim 2, wherein said second fluid is a substantially inert gas.

6. A method as defined in claim 5, wherein said second fluid is a gaseous fluid selected from the group comprising helium, argon and nitrogen.

7. A method as defined in claim 2, wherein said known time intervals are regular time intervals.

8. A probe for testing soil contamination, comprising:
   a rigid main body having an inner conduit, said inner conduit defining a lower opening and a first and a second top openings;

an inner tube which is coaxially located inside said inner conduit and of lesser diameter than said inner conduit, so as to allow fluid passage in said inner conduit about said tube, said inner tube extending upwardly out of said rigid main body through said inner conduit first top opening and defining a top opening outwardly of said rigid main body, said inner tube further defining a lower opening;

a seal mounted to said main body at said inner conduit first top opening, to prevent fluid passage out of said inner conduit through said inner conduit first top opening about said inner tube;

wherein either one of said inner conduit second top opening and said inner tube top opening is adapted to be connected to a circulation fluid source, while the other one of said inner conduit second top opening and said inner tube top opening is adapted to be connected to a fluid sample collecting device; and wherein said inner tube is axially slidable in said inner conduit between a retracted position, in which said inner tube lower opening is located inside said inner tube, and an extracted position, in which said inner tube lower opening projects out of and spacedly beyond said inner conduit lower opening, whereby fluid from said circulation fluid source is destined to circulate between said inner tube lower opening and said inner conduit lower opening which are spaced-apart.

9. A probe as defined in claim 8, wherein said tube is made of a semi-rigid plastic material.

10. A probe as defined in claim 8, wherein said inner tube lower opening is a number of spaced apart bores made at a bottom end portion of said tube.

* * * * *